(12) United States Patent
Wolfgang et al.

(10) Patent No.: US 8,999,638 B2
(45) Date of Patent: Apr. 7, 2015

(54) METHOD OF TREATMENT BASED ON POLYMORPHISMS OF THE KCNQ1 GENE

(75) Inventors: Curt D. Wolfgang, Germantown, MD (US); Mihael H. Polymeropoulos, Potomac, MD (US)

(73) Assignee: Vanda Pharmaceuticals, Inc., Washington, DC (US)

( * ) Notice: Subject to any disclaimer, the term of this patent is extended or adjusted under 35 U.S.C. 154(b) by 206 days.

(21) Appl. No.: 13/263,074

(22) PCT Filed: Apr. 5, 2010

(86) PCT No.: PCT/US2010/029921
§ 371 (c)(1),
(2), (4) Date: Oct. 5, 2011

(87) PCT Pub. No.: WO2010/117931
PCT Pub. Date: Oct. 14, 2010

(65) Prior Publication Data
US 2012/0027871 A1 Feb. 2, 2012

Related U.S. Application Data

(60) Provisional application No. 61/167,136, filed on Apr. 6, 2009.

(51) Int. Cl.
*C12Q 1/68* (2006.01)
*A61K 31/519* (2006.01)

(52) U.S. Cl.
CPC ............ *C12Q 1/6883* (2013.01); *A61K 31/519* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,364,866 A | 11/1994 | Strupczewski et al. | |
| 5,658,911 A | 8/1997 | Strupczewski et al. | |
| 6,140,345 A | 10/2000 | Strupczewski et al. | |
| 2006/0073506 A1 | 4/2006 | Christians et al. | |
| 2011/0077539 A1 | 3/2011 | George et al. | |

FOREIGN PATENT DOCUMENTS

| | | | | |
|---|---|---|---|---|
| WO | 9309276 | A1 | 5/1993 | |
| WO | 9511680 | A1 | 5/1995 | |
| WO | 0124681 | A2 | 4/2001 | |
| WO | 03016504 | A2 | 2/2003 | |
| WO | 03020707 | A1 | 3/2003 | |
| WO | 03062791 | A2 | 7/2003 | |
| WO | 2004057030 | A2 | 7/2004 | |
| WO | 2006039663 | A2 | 4/2006 | |
| WO | WO2006/009663 | * | 4/2006 | ........................ 435/6 |
| WO | 2006039663 | A3 | 11/2006 | |
| WO | 2006124646 | A2 | 11/2006 | |
| WO | 2006131528 | A2 | 12/2006 | |
| WO | 2006131528 | A3 | 3/2007 | |
| WO | 2006124646 | A3 | 8/2007 | |

OTHER PUBLICATIONS

Juppner; Bone, vol. 17; 1995, pp. 39S-40S.*
Lucentini (The Scientist; 2004, vol. 24, p. 20).*
Hegele (Arterioscler. Thromb. Vasc. Biol.; 2002, vol. 22, pp. 1058-1061).*
Volpi et al; 57th Annual meeting of the American Society of Human Genetics, 2007, Abstract.*
Levine et al; Formulary Journal, Jun. 1, 2008, pp. 1-7.*
Genbank Accession No. AJ006345.1, NCBI, NLM; 2006).*
Cussac, International Application No. PCT / US2010 / 029931, PCT International Preliminary Report on Patentability, dated Apr. 6, 2009, 7 pages.
Nickitas-Etienne, International Application No. PCT / US2010 / 029945, PCT International Preliminary Report on Patentability, dated Apr. 6, 2009, 7 pages.
Nickitas-Etienne, International Application No. PCT / US2010 / 029943, PCT International Preliminary Report on Patentability, dated Apr. 6, 2009, 7 pages.
Lindner, International Application No. PCT / US2010 / 029921, PCT International Preliminary Report on Patentability, dated Apr. 6, 2009, 7 pages.
Chiang et al., "The Long QT Syndromes: Genetic Basis and Clinical Implications," Jul. 2000, pp. 1-12, Journal of American College of Cardiology, vol. 36, Nol 1 (XP002590440).
Donger et al., "KVLQT1 C-Terminal Missense Mutation Causes a Forme Fruste Long-QT Syndrome," Nov. 1997, pp. 2778-2781, American Heart Association, vol. 96, No. 9 (XP002922668).
Liu et al., "KCNQ1 and KCNH2 Mutations Associated with Long QT Syndrome in a Chinese Population," Nov. 2002, pp. 1-7, Human Mutation, Mutation in Brief, vol. 20, No. 6 (XP002590441).
Volpi et al., "Whole Genome Association Study Identifies Polymorphisms Associated with QT Prolongation During Iloperidone Treatment of Schizophrenia," Jun. 2008, pp. 1024-1031, Molecular Psychiatry, vol. 14, No. 11 (XP002590482).
Yang et al., "Allelic Variants in Long-QT Disease Genes in Patients With Drug-Associated Torsades de Pointes," Apr. 2002, pp. 1943-1948, Circulation downloaded from: circ.ahajournals.org at the European Patent Office.
Patent Cooperation Treaty, PCT Notification of Transmittal of the International Search Report and The Written Opinion of the International Searching Authority, or the Declaration for PCT/US2010/029921 dated Aug. 19, 2010, 15 pages.
Cohen et al., "Cloning and Characterization of FAM13A1—A Gene Near a Milk Protein QTL on BTA6: Evidence for Population-Wide Linkage Disequilibrium in Israeli Holsteins," Aug. 2004, pp. 374-383, Genomics 84, Academic Press, available online at: www.sciencedirect.com.
Patent Cooperation Treaty, PCT Notification of Transmittal of The International Search Report and The Written Opinion of the International Searching Authority, or the Declaration for PCT/US2010/029931 dated May 27, 2010, 13 pages.

(Continued)

*Primary Examiner* — Jehanne Sitton
(74) *Attorney, Agent, or Firm* — Hoffman Warnick LLC

(57) ABSTRACT

The invention provides methods for the administration of compounds capable of prolonging a QTc interval and methods for predicting whether an individual is predisposed to such QTc prolongation.

15 Claims, No Drawings

(56) References Cited

OTHER PUBLICATIONS

Cascorbi, "Role of Pharmacogenetics of ATP-Binding Cassette Transporters in the Pharmacokinetis of Drugs," Nov. 2006, pp. 457-473, Pharmacology & Therapeutics, Science Direct, vol. 112, No. 2.
Patent Cooperation Treaty, PCT Notification of Transmittal of The International Search Report and The Written Opinion of the International Searching Authority, or the Declaration for PCT/US2010/029943 dated Jul. 5, 2010, 14 pages.
Fujita et al., "Association of ATP-Binding Cassette, Sub-Family C, No. 2 (ABCC2) Genotype with Pharmacokinetics of Irinotecan in Japanese Patients with Metastatic Colorectal Cancer Treated with Irinotecan Plus Infusional 5-Fluorouracil/Leucovorin (FOLFIRI)," Nov. 2008, pp. 2137-2142, Biological & Pharmaceutical Bulletin, vol. 31, No. 11 (XP007913544).
Derosse et al., "The Genetics of Symptom-Based Phenotypes: Toward a Molecular Classification of Schizophrenia," Jul. 2008, pp. 1047-1043, Schizophrenia Bulletin, vol. 34, No. 6 (XP007913527).
Patent Cooperation Treaty, PCT Notification of Transmittal of The International Search Report and The Written Opinion of the International Searching Authority, or the Declaration for PCT/US2010/029945 dated Jul. 7, 2010, 13 pages.
Juppner, "Functional Properties of the PTH/PTHrP Receptor," 1995, pp. 39S-42S, Bone, vol. 17, No. 2.
Levine et al., "Iloperidone: A novel atypical antipsychotic for the treatment of schizophrenia," 2008, pp. 1-7, Formulary Journal.
Lucentini, "Gene Association Studies Typically Wrong," 2004, p. 20, The Scientist, vol. 24.
Hegele, "SNP Judgments and Freedom of Association," 2003, pp. 1058-1061, Arteriosclerosis, Thrombosis, and Vascular Biology, vol. 22.
Volpi et al., "Pharmacogenomic analysis shows differences between markers associated with responses of two atypical antipsychotics, iloperidone and ziprasidone, in the treatment of patients with schizophrenia," 2007, Abstsract, 57 Annual Meeting of the American Society of Human Genetics.
ss66324480, rs3775378, dbSNP Short Genetic Variations, NCBI, NLM, 2006, 5 pages.
ss66391863, rs7067971, dbSNP Short Genetic Variations, NCBI, NLM, 2006, 3 pages.
ss66046634, rs1083338, dbSNP Short Genetic Variations, NCBI, NLM, 2007, 5 pages.
Sitton, Office Action Communication for U.S. Appl. No. 13/263,075 dated Oct. 8, 2013, 23 pages.
Sitton, Office Action Communication for U.S. Appl. No. 13/263,076 dated Nov. 29, 2013, 24 pages.
Sitton, Office Action Communication for U.S. Appl. No. 13/263,077 dated Nov. 7, 2013, 25 pages.
Mueller, Frank, Patent Application No. 10713287.0 Office Action dated Jun. 11, 2014, 6 pages.
Sitton, Office Action Communication for U.S. Appl. No. 13/263,075 dated Mar. 20, 2014, 11 pages.
Sitton, Office Action Communication for U.S. Appl. No. 13/263,076 dated Mar. 27, 2014, 11 pages.
Sitton, Office Action Communication for U.S. Appl. No. 13/263,077 dated Mar. 27, 2014, 11 pages.

* cited by examiner

METHOD OF TREATMENT BASED ON POLYMORPHISMS OF THE KCNQ1 GENE

CROSS-REFERENCE TO RELATED APPLICATIONS

This application claims the benefit of U.S. Provisional Patent Application No. 61/167,136, filed 6 Apr. 2009, which is hereby incorporated here.

SEQUENCE LISTING

The sequence listing contained in the electronic file titled "VAND-0039-US_Seq_ID_6-12-2014_Cleartxt" created Jun. 12, 2014, comprising 995 KB, is hereby incorporated by reference herein.

BACKGROUND OF THE INVENTION

1. Technical Field

The invention relates generally to the administration of antipsychotics, and more particularly, to the administration of antipsychotics based on an individual's KCNQ1 genotype.

2. Background

Prolongation of the electrocardiographic QT interval (the time between the start of the Q wave and the end of the T wave) is referred to as long QT syndrome (LQTS). LQTS may comprise a genetic component. In some patients with LQTS, QT prolongation can be a chronic condition. In some persons, LQTS may be induced by the administration of an active pharmaceutical ingredient that prolongs the QT interval.

An area of focus in the evaluation of drug safety is the effect of non-cardiac medications on the QT interval. It is thought that the primary mechanism of action by which non-cardiac medications prolong the duration of the QT interval is through inhibition of the Human Ether-a-go-go related Gene (HERG) channel, a potassium channel directly involved in ventricular repolarization. QT prolongation and its relationship to torsades de pointes arrhythmia has received increased attention from regulatory authorities, resulting in warnings on the labels of some antipsychotics.

Since the QT interval changes with changes in heart rate, the QT interval is often measured as a corrected QT (QTc) interval. Any number of formulas may be employed to calculate the QTc, including, for example, the Fridericia formula (QTcF), the Bazett formula (QTcB), and the Rautaharju formula (QTp), among others.

DNA variants in potassium voltage-gated channels, such as KCNQ1, have been identified to predispose patients to drug-associated "acquired" LQTS and are considered congenital LQTS genes.

The KCNQ1 gene encodes a protein for a voltage-gated potassium channel required for the repolarization phase of the cardiac action potential. The gene product can form heteromultimers with two other potassium channel proteins, KCNE1 and KCNE3. Mutations in the KCNQ1 gene are associated with hereditary LQTS, Romano-Ward syndrome, Jervell and Lange-Nielsen syndrome, and familial atrial fibrillation. The gene is located in a region of chromosome 11 that contains a large number of contiguous genes that are abnormally imprinted in cancer and the Beckwith-Wiedemann syndrome.

KCNQ1 alpha-subunits coassemble with KCNE1 beta-subunits to form channels that conduct the slow delayed rectifier K+ current (IKs) important for repolarization of the cardiac action potential. Mutations in KCNQ1 reduce IKs and cause LQTS.

Antipsychotics, both typical and atypical, have been associated with an increase in the duration of the QTc interval. A study comparing the effect of several antipsychotics on the QTc duration showed thioridazine to be associated with the highest degree of QTc prolongation, followed by ziprasidone. Quetiapine, risperidone, olanzapine, and haloperidol were also associated with a prolongation of the QTc interval. In this study, minimum increase in QTc was observed when metabolic inhibitors of the CYP450 isoenzyme responsible for the metabolism of each respective drug, except for haloperidol, which resulted in a doubling of QTc with metabolic inhibition.

As has been seen with other antipsychotics, iloperidone has been observed to have some effects on QTc duration. Iloperidone is metabolized by CYP2D6. Metabolic inhibition by adding an inhibitor of CYP2D6 increases the effect of iloperidone on the QTcF duration. Methods for the administration of iloperidone based on an individual's CYP2D6 genotype are described in International Patent Application Publication No. WO2006039663, which is incorporated herein.

In addition to iloperidone, a number of other compounds are believed to be capable of causing QT prolongation. These include amiodarone, arsenic trioxide, bepridil, chloroquine, chlorpromazine, cisapride, clarithromycin, disopyramide, dofetilide, domperidone, droperidol, erythromycin, halofantrine, haloperidol, ibutilide, levomethadyl, mesoridazine, methadone, pentamidine, pimozide, procainamide, quinidine, sotalol, sparfloxacin, and thioridazine.

Other compounds, in addition to ziprasidone, are suspected of being capable of prolonging the QT interval, although such prolongation has not been definitively established. These include alfuzosin, amantadine, azithromycin, chloral hydrate, clozapine, dolasetron, felbamate, flecainide, foscarnet, fosphenytoin, gatifloxacin, gemifloxacin, granisetron, indapamide, isradipine, levofloxacin, lithium, moexipril, moxifloxacin, nicardipine, octreotide, ofloxacin, ondansetron, quetiapine, ranolazine, risperidone, roxithromycin, tacrolimus, tamoxifen, telithromycin, tizanidine, vardenafil, venlafaxine, and voriconazole.

Individuals at risk of suffering LQTS are advised not to use still other compounds, due to the possibility that they may prolong the QT interval. These include albuterol, amitriptyline, amoxapine, amphetamine, dextroamphetamine, atomoxetine, chloroquine, ciprofloxacin, citalopram, clomipramine, cocaine, desipramine, dexmethylphenidate, dobutamine, dopamine, doxepin, ephedrine, epinephrine, fenfluramine, fluconazole, fluoxetine, galantamine, imipramine, isoproterenol, itraconazole, ketoconazole, levalbuterol, metaproterenol, methylphenidate, mexiletine, midodrine, norepinephrine, nortriptyline, paroxetine, phentermine, phenylephrine, phenylpropanolamine, protriptyline, pseudoephedrine, ritodrine, salmeterol, sertraline, sibutramine, solifenacin, terbutaline, tolterodine, trimethoprim-sulfa, and trimipramine.

SUMMARY OF THE INVENTION

The invention provides methods for the administration of compounds capable of prolonging a QTc interval and methods for predicting whether an individual is predisposed to such QTc prolongation.

A first aspect of the invention provides a method of treating a patient with a compound capable of prolonging the QT interval, the method comprising: determining at least a portion of the patient's KCNQ1 gene sequence; and administering to the patient a quantity of the compound based on the patient's KCNQ1 gene sequence. In some embodiments, the method further includes determining at least a portion of the patient's CYP2D6 gene sequence.

A second aspect of the invention provides a method of determining whether an individual is predisposed to prolongation of the QTc interval, the method comprising: determining at least a portion of an individual's KCNQ1 gene sequence.

A third aspect of the invention provides a method of treating a patient with a compound capable of prolonging the QT interval, the method comprising: characterizing an expression product of the patient's KCNQ1 gene; and administering to the patient a quantity of the compound based on the characterized expression product.

A fourth aspect of the invention provides a method of determining whether an individual is predisposed to prolongation of the QTc interval, the method comprising: characterizing an expression product of an individual's KCNQ1 gene.

The illustrative aspects of the present invention are designed to solve the problems herein described and other problems not discussed, which are discoverable by a skilled artisan.

DETAILED DESCRIPTION

As indicated above, the invention provides methods for the administration of antipsychotics based on an individual's KCNQ1 genotype. The sequence of wild type KCNQ1 (GenBank Accession No. AJ006345.1) is provided herein as SEQ. ID. 1.

As noted above, a large number of compounds are known or suspected to be capable of inducing QT prolongation in some individuals, including individuals not suffering from LQTS. Such compounds may include compounds of Formula (1):

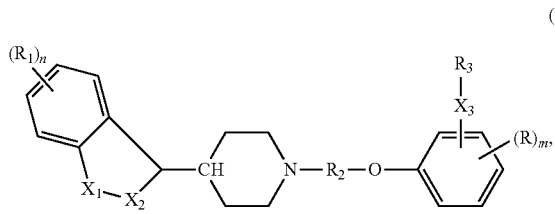

wherein:

R is, independently, hydrogen, lower alkyl, lower alkoxy, hydroxyl, carboxyl, lower hydroxyketone, lower alkanol, hydroxyl acetic acid, pyruvic acid, ethanediol, chlorine, fluorine, bromine, iodine, amino, lower mono or dialkylamino, nitro, lower alkyl thio, trifluoromethoxy, cyano, acylamino, trifluoromethyl, trifluoroacetyl, aminocarbonyl, monoakylaminocarbonyl, dialkylaminocarbonyl, formyl,

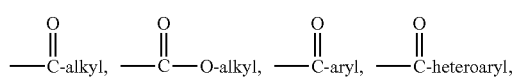

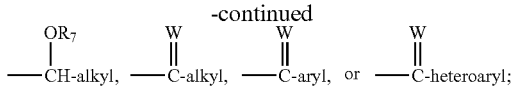

alkyl is lower alkyl, branched or straight and saturated or unsaturated;

acyl is lower alkyl or lower alkyloxy bonded through a carbonyl:

aryl is phenyl or phenyl substituted with at least one group, $R_5$, wherein each $R_5$ is, independently, hydrogen, lower alkyl, lower alkoxy, hydroxy, chlorine, fluorine, bromine, iodine, lower monoalkylamino, lower dialkylamino, nitro, cyano, trifluoromethyl, or trifluoromethoxy;

heteroaryl is is a five- or six-membered aryl ring having at least one heteroatom, $Q_3$, wherein each $Q_3$ is, independently, —O—, —S—, —N(H)—, or —C(H)=N—

W is $CH_2$ or $CHR_8$ or N—$R_9$;

$R_1$ is —H, lower alkyl, —OH, halo, lower alkoxy, trifluormethyl, nitro, or amino;

$R_2$ is $C_2$-$C_5$ alkylene, alkenylene (cis or trans), or alkynylene, optionally substituted by at least one $C_1$-$C_6$ linear alkyl group, phenyl group or

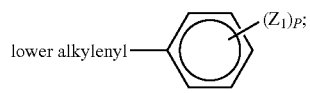

where $Z_1$ is lower alkyl, —OH, lower alkoxy, —$CF_3$, —$NO_2$, —$NH_2$, or halogen;

$R_3$ is lower alkyl or hydrogen;

$R_7$ is hydrogen, lower alkyl, or acyl;

$R_8$ is lower alkyl;

$R_9$ is hydroxy, lower alkoxy, or —$NHR_{10}$;

$R_{10}$ is hydrogen, lower alkyl, $C_1$-$C_3$ acyl, aryl,

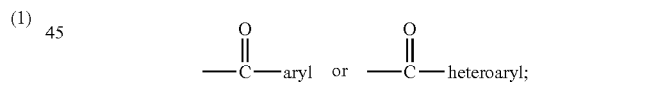

$X_1$, $X_2$, and $X_3$ are, independently, —O—, —S—, =N—, or —N($R_3$)—, or $X_1$ and $X_2$ are not covalently bound to each other and are, independently, —OH, =O, —$R_3$, or =$NR_3$;

lower is 1-4 carbon atoms;

m is 1, 2, or 3; and n is 1 or 2.

The compound may further include a compound of Formula (1) wherein:

R is —C(O)$CH_2$OH, —CH(OH)C(O)$CH_2$OH, —C(O)OH, CH(OH)$CH_3$, or C(O)$CH_3$;

$R_1$ is halo;

$X_1$ and $X_2$ are different and are =O, —OH, =N—, or —O—;

$R_2$ is $C_2$-$C_4$ alkylene or alkenylene;

$R_3$ is hydrogen, methyl, or ethyl;

$X_3$ is —O—; and

R is substituted as shown in Formula 1A

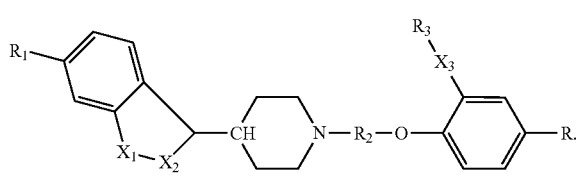

(1A)

In a further embodiment, the compound may be iloperidone, which is also referred to as 1-[4-[3-[4-(6-fluoro-1,2-benzisoxazol-3-yl)-1-piperidinyl]propoxy]-3-methoxyphenyl]ethanone, as shown in Formula 1B:

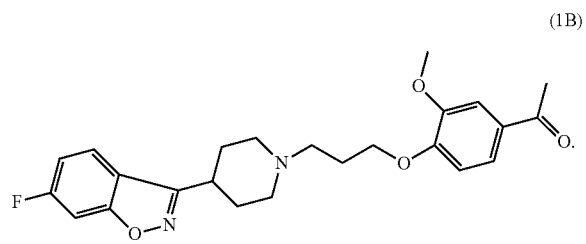 [SMILES: COc1cc(C(C)=O)ccc1OCCCN1CCC(c2noc3cc(F)ccc23)CC1]

(1B)

Iloperidone is disclosed in U.S. Pat. Nos. 5,364,866, 5,658,911, and 6,140,345, each of which is incorporated herein by reference. Metabolites of iloperidone may also be capable of prolonging a QT interval. Metabolites of Iloperidone, e.g., 1-[4-[3-[4-(6-Fluoro-1,2-benzisoxazol-3-yl)-1-piperidinyl] propoxy]-3-methoxyphenyl]ethanol, as shown in Formula 1C:

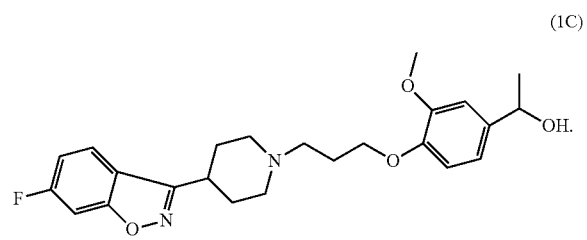 [SMILES: COc1cc(C(C)O)ccc1OCCCN1CCC(c2noc3cc(F)ccc23)CC1]

(1C)

are described in International Patent Application Publication No. WO03020707, which is also incorporated herein by reference. Other iloperidone metabolites include: 1-[4-[3-[4-(6-Fluoro-1,2-benzisoxazol-3-yl)-1-piperidinyl]propoxy]-3-hydroxyphenyl]ethanone; 1-[4-[3-[4-(6-Fluoro-1,2-benzisoxazol-3-yl)-1-piperidinyl]propoxy]-3-methoxyphenyl]-2-hydroxyethanone; 4-[3-[4-(6-Fluoro-1,2-benzisoxazol-3-yl)-1-piperidinyl]propoxy]-3-hydroxy-α-methylbenzene methanol; 4-[3-[4-(6-Fluoro-1,2-benzisoxazol-3-yl)-1-piperidinyl]propoxyl-2-hydroxy-5-methoxy-α-methylbenzenemethanol; 1-[4-[3-[4-(6-Fluoro-1,2-benzisoxazol-3-yl)-1-piperidinyl]propoxy]-2-hydroxy-5-methoxyphenyl]ethanone; and 1-[4-[3-[4-(6-Fluoro-1,2-benzisoxazol-3-yl)-1-piperidinyl]propoxy]-2,5-dihydroxyphenyl]ethanone. See U.S. Pat. No. 5,364,866 and International Patent Application Publication Nos. WO9309276 and WO9511680, which are incorporated herein by reference.

The DNA variants in KCNQ1 noted above were examined for correlation with iloperidone-induced QT prolongation. These single nucleotide polymorphisms (SNPs) are shown in Table 1, below. The sequence of KCNQ1 (GenBank Accession No. AJ006345.1) having a C to G mutation at position 79764 is provided herein as SEQ. ID. 2.

TABLE 1

| KCNQ1 SNPs Linked to Acquired LQTS | | |
|---|---|---|
| Genbank Accession No. | Position | Mutation |
| AJ006345.1 | 79764 | C to G |
| AJ006345.1 | 286414 | G to A |
| AJ006345.1 | 78927 | A to C |

Individuals from an earlier study of CYP2D6 genotypes and a predisposition to QT prolongation were genotyped at each of the KCNQ1 SNPs above. 22 individuals had been given a dose of 8 mg of iloperidone b.i.d., 30 had been given 12 mg b.i.d., and 22 had been given 24 mg q.d.

Results for the position 79764 SNP are shown below in Tables 2 and 3. As can be seen, individuals homozygous for the C>G polymorphism showed a significantly greater increase in QTc interval following the administration of iloperidone. In fact, the average QTc change in individuals with the GG genotype was more than twice the change in individuals with a non-GG genotype.

TABLE 2

79764 SNP Genotype and QTcF Change Following Iloperidone Administration

| Genotype | n | QTcF change (msec) |
|---|---|---|
| CC | 13 | 10.38 |
| CG | 32 | 6.80 |
| GG | 26 | 17.58 |

TABLE 3

79764 SNP Genotype and QTcF Change Following Iloperidone Administration

| Genotype | n | QTcF change (msec) | P value |
|---|---|---|---|
| Non-GG | 45 | 7.83 | 0.0008 |
| GG | 26 | 17.58 | |

The results were similar when ziprasidone was administered at a dosage of 80 mg b.i.d. The QTc changes for each genotype are shown below in Tables 4 and 5.

TABLE 4

79764 SNP Genotype and QTcF Change Following Ziprasidone Administration

| Genotype | n | QTcF change (msec) |
|---|---|---|
| CC | 5 | 8.30 |
| CG | 14 | 6.19 |
| GG | 6 | 15.32 |

TABLE 5

79764 SNP Genotype and QTcF Change Following Ziprasidone Administration

| Genotype | n | QTcF change (msec) | P value |
|---|---|---|---|
| Non-GG | 19 | 6.75 | 0.084 |
| GG | 6 | 15.32 | |

Similar results were observed for the 286414 position SNP, the results of which are shown below in Tables 6 and 7. Individuals homozygous for the G>A polymorphism experienced average QTc increases more than double those experienced by individuals with a non-AA genotype.

TABLE 6

286414 position SNP Genotype and QTcF Change Following Iloperidone Administration

| Genotype | n | QTcF change (msec) |
|---|---|---|
| AA | 32 | 12.50 |
| AG | 18 | 3.15 |
| GG | 7 | 10.34 |

TABLE 7

286414 position SNP Genotype and QTcF Change Following Iloperidone Administration

| Genotype | n | QTcF change (msec) | P value |
|---|---|---|---|
| AA | 32 | 12.51 | 0.0268 |
| Non-AA | 25 | 5.16 | |

The 78927 position SNP also yielded similar results, shown below in Tables 8 and 9. Again, individuals homozygous for the A>C polymorphism experienced average QTc increases more than double those experienced by individuals with a non-CC genotype.

TABLE 8

78927 position SNP Genotype and QTcF Change Following Iloperidone Administration

| Genotype | n | QTcF change (msec) |
|---|---|---|
| AA | 10 | 7.21 |
| AC | 31 | 9.19 |
| CC | 33 | 14.08 |

TABLE 9

78927 position SNP Genotype and QTcF Change Following Iloperidone Administration

| Genotype | n | QTcF change (msec) | P value |
|---|---|---|---|
| Non-CC | 41 | 6.46 | 0.057 |
| CC | 33 | 14.08 | |

As noted above, and as described in International Patent Application Publication No. WO2006/039663, an individual's ability to metabolize iloperidone may be predicted based on his/her CYP2D6 genotype. The CYP2D6 gene is highly polymorphic, with more than 70 allelic variants described so far (see http://www.cypalleles.ki.se/).

The two most common polymorphisms within the CYP2D6 gene in Caucasian populations, CYP2D6G1846A and CYP2D6C100T, result in a "poor metabolizer" phenotype and thus higher circulating drug levels in the blood. The CYP2D6G1846A polymorphism represents a G to A transition at the junction between intron 3 and exon 4, shifting the splice junction by one base pair, resulting in frameshift and premature termination of the protein. The CYP2D6C100T polymorphism, also known as CYP2D6P34S, represents a C to T change that results in the substitution of a proline at position 34 by serine. Both of these polymorphisms have been associated with reduced enzymatic activity for different substrates.

Interestingly, a relationship was found between the KCNQ1 polymorphisms above and an individual's metabolizer status (i.e., "extensive," "intermediate," or "poor"), as predicted by whether the individual has one or both of the CYP2D6G1846A and CYP2D6C100T polymorphisms.

Tables 10 and 11 below show CYP2D6 metabolizer status against QTcFmax change from baseline for individuals having GG and non-GG genotypes, respectively, at the KCNQ1 79764 position SNP.

TABLE 10

QTcF Change in Individuals Having KCNQ1 79764 Position SNP Genotype GG and Varying CYP2D6 Metabolizer Status

| CYP2D6 Metabolizer Status | n (%) | QTcFmax Change (msec) |
|---|---|---|
| Extensive | 17 (65%) | 16.4 |
| Intermediate | 8 (31%) | 18.1 |
| Poor | 1 (4%) | 33.6 |

TABLE 11

QTcF Change in Individuals Having KCNQ1 79764 Position SNP Genotype Non-GG and Varying CYP2D6 Metabolizer Status

| CYP2D6 Metabolizer Status | n (%) | QTcFmax Change (msec) |
|---|---|---|
| Extensive | 37 (82%) | 8.3 |
| Intermediate | 7 (16%) | 3.1 |
| Poor | 1 (2%) | 24.6 |

As can be seen, individuals who are GG at the 79764 SNP experience greater QTc prolongation than do individuals who are non-GG. In addition, within each group, and particularly among GG individuals, CYP2D6 metabolizer status is highly predictive of the relative degree of QTc prolongation an individual will experience. Thus, an individual who is GG at the KCNQ1 79764 SNP and a CYP2D6 poor metabolizer may be administered a lower dose of iloperidone or other QT-prolonging compound, due to the individual's greater likelihood of experiencing more severe QT prolongation. Alternatively, the individual may instead be administered a compound not known or suspected of causing QT prolongation.

In order to assess the CYP2D6 component to such prolongation, QTc change was separately compared to the CYP2D6G1846A and CYP2D6C100T polymorphisms. These results are shown below in Tables 12 and 13. As can be seen, individuals homozygous for the wild-type allele (G for CYP2D6G1846A and C for CYP2D6C100T) experienced less QT prolongation than did individuals having one or two mutant alleles (A for CYP2D6G1846A and T for CYP2D6C100T).

TABLE 12

CYP2D6G1846A Polymorphism Compared to QTc Change Following Iloperidone Administration

| Genotype | n | QTcF change (msec) | P value |
|---|---|---|---|
| GG | 52 | 11.1 | |
| AG | 14 | 15.9 | |
| AA | 2 | 41.6 | |
| GG | 52 | 11.1 | 0.0594 |
| Non-GG | 16 | 18.5 | |

TABLE 13

CYP2D6C100T Polymorphism Compared to QTc Change Following Iloperidone Administration

| Genotype | n | QTcF change (msec) | P value |
|---|---|---|---|
| CC | 54 | 10.8 | |
| CT | 14 | 16.9 | |
| TT | 3 | 31.3 | |
| CC | 54 | 10.8 | 0.0281 |
| Non-CC | 17 | 19.2 | |

Tables 14 and 15 below show QTc changes in individuals grouped according to their KCNQ1 79764, CYP2D6G1846A, and CYP2D6C100T genotypes. This shows that individuals who were non-GG at KCNQ1 79764 and were homozygous for the wild-type allele at the CYP2D6 loci (i.e., GG for CYP2D6G1846A and CC for CYP2D6C100T) experienced the least QT prolongation. Similarly, individuals who were GG at KCNQ1 79764 and had one or two mutant alleles at the CYP2D6 loci (i.e., AG or AA at CYP2D6G1846A and CT or TT at CYP2D6C100T) experienced the greatest QT prolongation.

This may make it possible, for example, to manage the risk associated with the administration of compounds capable of prolonging the QTc interval. Individuals possessing only the wild-type alleles at the KCNQ1 and CYP2D6 loci may reasonably be expected to experience relatively little QTc prolongation while individuals possessing one or more mutant alleles may be expected to experience greater QTc prolongation, with the extent of prolongation increasing with an increasing number of mutant alleles. Individuals would then be administered a dosage of the compound based on his/her KCNQ1 and/or CYP2D6 genotypes or may be administered another compound instead that is not known or suspected of prolonging the QTc interval.

The data in Tables 14 and 15 also suggest that KCNQ1 polymorphisms have a greater impact on QTc prolongation than do the CYP2D6 polymorphisms. This may provide greater detail in the risk management, testing, and treatment methods above.

TABLE 14

QTcF Change Compared to KCNQ1 79764 and CYP2D6G1846A Genotypes Following Iloperidone Administration

| | QTcF change (msec) | |
|---|---|---|
| KCNQ1 79764 non-GG | 7.6 (n = 34) | 9.6 (n = 6) |
| KCNQ1 79764 GG | 19.5 (n = 15) | 25.5 (n = 10) |
| | CYP2D6G1846A GG | CYP2D6G1846A non-GG |

TABLE 15

QTcF Change Compared to KCNQ1 79764 and CYP2D6C100T Genotypes Following Iloperidone Administration

| | QTcF change (msec) | |
|---|---|---|
| KCNQ1 79764 non-GG | 7.4 (n = 35) | 12.6 (n = 7) |
| KCNQ1 79764 GG | 19.2 (n = 15) | 23.5 (n = 10) |
| | CYP2D6C100T CC | CYP2D6C100T non-CC |

Additional KCNQ1 SNPs were examined for any correlation to a predisposition to QTc prolongation. Those SNPs are shown below in Table 16. SNPs useful in the practice of the invention include those listed above and in Table 16 below, and can be used singly or in any combination of two or more.

TABLE 16

KCNQ1 SNP Genotypes and QT Prolongation Following Administration of Iloperidone

| Affymetrix SNP No. | rs_number[1] | Position[2] | Lowest QTc change | P value[3] | Allele A | Allele B |
|---|---|---|---|---|---|---|
| SNP_A-1861793 | rs234873 | 2764098 | nonAA | 0.110421 | C | T |
| SNP_A-1905847 | rs233446 | 2794201 | nonAA | 0.12044 | A | C |
| SNP_A-1905948 | rs179428 | 2507085 | nonAA | 0.548076 | A | G |
| SNP_A-2063010 | rs10832134 | 2459062 | AA | 0.613499 | C | T |
| SNP_A-2070173 | rs10832405 | 2605095 | nonAA | 0.421724 | G | T |
| SNP_A-2128672 | rs10798 | 2826741 | nonAA | 0.149325 | C | T |
| SNP_A-2138827 | rs548566 | 2739224 | AA | 0.533236 | A | G |
| SNP_A-2155585 | rs231915 | 2705591 | nonAB | 0.811901 | A | G |
| SNP_A-2170993 | rs170786 | 2707279 | BB | 0.609952 | C | T |
| SNP_A-2176134 | rs10766379 | 2782775 | BB | 0.149903 | A | G |
| SNP_A-2203798 | rs8181588 | 2788117 | nonBB | 0.486341 | A | G |
| SNP_A-2217853 | rs179429 | 2507306 | BB | 0.323283 | C | T |
| SNP_A-2244304 | rs7128926 | 2653320 | AB | 0.074244 | C | T |
| SNP_A-2264175 | rs6578283 | 2630151 | BB | 0.385571 | A | G |
| SNP_A-2299737 | rs163177 | 2794989 | AA | 0.03059 | A | G |
| SNP_A-2301145 | rs163166 | 2781804 | BB | 0.147875 | G | T |
| SNP_A-2305877 | rs231916 | 2704944 | nonAB | 0.033582 | A | G |
| SNP_A-4241656 | rs231907 | 2708706 | nonBB | 0.802946 | A | T |
| SNP_A-4242308 | rs2283208 | 2700435 | AA | 0.019908 | A | G |

TABLE 16-continued

KCNQ1 SNP Genotypes and QT Prolongation
Following Administration of Iloperidone

| Affymetrix SNP No. | rs_number[1] | Position[2] | Lowest QTc change | P value[3] | Allele A | Allele B |
|---|---|---|---|---|---|---|
| SNP_A-4248246 | — | 2667398 | nonAA | 0.381774 | C | T |
| SNP_A-4254887 | rs231348 | 2630257 | nonBB | 0.626472 | A | G |
| SNP_A-4257005 | rs16928297 | 2442696 | AA | 0.483607 | G | T |
| SNP_A-4281714 | rs3852527 | 2783179 | nonAA | 0.197306 | A | G |
| SNP_A-4288131 | rs231890 | 2732635 | nonAB | 0.573 | C | T |
| SNP_A-4288827 | rs10766218 | 2594657 | AA | 0.357049 | A | G |
| SNP_A-4301076 | rs163171 | 2777641 | nonAB | 0.259187 | C | T |
| SNP_A-4301585 | rs9666537 | 2642440 | nonBB | 0.262343 | C | T |
| SNP_A-4302062 | rs1971929 | 2729947 | AA | 0.611517 | C | G |
| SNP_A-4302119 | rs3852528 | 2783193 | nonBB | 0.041388 | A | G |
| SNP_A-1819033 | rs151291 | 2731415 | nonAA | 0.260891 | C | T |
| SNP_A-1824380 | rs179409 | 2483882 | AA | 0.310425 | C | G |
| SNP_A-1829337 | rs231873 | 2742118 | nonAB | 0.422393 | C | G |
| SNP_A-1845199 | rs2412058 | 2597705 | AA | 0.29063 | C | T |
| SNP_A-1866128 | rs12804445 | 2834275 | BB | 0.431295 | A | C |
| SNP_A-2045452 | rs7942590 | 2590291 | AA | 0.7495 | C | G |
| SNP_A-2078818 | rs4430486 | 2741967 | BB | 0.177528 | C | G |
| SNP_A-2089816 | rs10741669 | 2600056 | nonAB | 0.154721 | C | T |
| SNP_A-2108877 | rs10766212 | 2589728 | AA | 0.181241 | A | G |
| SNP_A-2111327 | rs11517737 | 2481124 | nonAB | 0.612965 | A | G |
| SNP_A-2115624 | rs4930013 | 2818735 | AB | 0.762452 | G | T |
| SNP_A-2139714 | rs4930149 | 2692602 | AA | 0.42212 | A | C |
| SNP_A-2147212 | rs11023096 | 2484579 | BB | 0.011594 | A | G |
| SNP_A-2167641 | rs7927129 | 2672108 | nonAA | 0.905521 | A | C |
| SNP_A-2185200 | rs231901 | 2687761 | AA | 0.399107 | C | T |
| SNP_A-2188014 | rs2237866 | 2486738 | AA | 0.016676 | C | T |
| SNP_A-2199433 | rs12576156 | 2455394 | nonAA | 0.055461 | C | T |
| SNP_A-2207071 | rs163183 | 2801017 | nonBB | 0.080842 | A | G |
| SNP_A-2222217 | rs231841 | 2680180 | AB | 0.041003 | A | C |
| SNP_A-2248126 | rs3819506 | 2484900 | BB | 0.043565 | A | G |
| SNP_A-2279904 | rs16928561 | 2672031 | BB | 0.222103 | A | G |
| SNP_A-2279707 | rs179407 | 2483474 | nonBB | 0.011184 | C | T |
| SNP_A-2281097 | rs1079714 | 2717317 | nonBB | 0.583124 | C | T |
| SNP_A-2286096 | rs11023094 | 2483937 | nonAB | 0.158471 | C | T |
| SNP_A-2306355 | rs17744869 | 2780438 | nonBB | 0.236986 | C | G |

[1]Official SNP nomenclature according to NCBI db SNP version 126, May 2006.
[2]Chromosomal position based on the NCBI Build 36.1, March 2006.
[3]P value of genotype having highest QT values versus all other genotypes.

Among the SNPs shown in Table 16, a genotype of TT at SNP_A-2279707 (rs179407) was shown to accurately predict a predisposition to QTc prolongation. Therefore, an individual having a genotype of TT at SNP_A-2279707 (rs179407) may be predicted to be predisposed to QTc prolongation.

Table 17 below shows the results of a study of 174 individuals, each of whom was genotyped at the rs179407 locus and their QT interval measured following the oral administration of 24 mg/day B.I.D. of iloperidone for a period of two weeks.

example, using the lowest threshold of a change in QTc interval (between baseline and the end of the second week) greater than 5 milliseconds (normal QTc intervals are between 0.30 and 0.44 seconds for males and between 0.30 and 0.45 for females), 102 of those individuals with a SNP genotype (test is considered positive if genotype for SNP_A-2279707 (rs179407) is TT) associated with a predisposition to QT prolongation experienced QT prolongation while only 47 such individuals did not. Similarly, nearly seven times as many individuals (102) experiencing QT prolongation possessed a SNP genotype associated with a predisposition to QT

TABLE 17

QT Prolongation and Presence or Absence of a Genotype for SNP_A-2279707
(rs179407) Associated with a Predisposition to QT Prolongation

| Change Threshold (msec) | Low QT −test | Low QT +test | High QT −test | High QT +test | Odds Ratio | p value | sensitivity | specificity | negative predictive value | positive predictive value |
|---|---|---|---|---|---|---|---|---|---|---|
| QT > 5 | 19 | 47 | 15 | 102 | 2.748936 | 0.0091 | 0.871795 | 0.287879 | 0.558824 | 0.684564 |
| QT > 15 | 25 | 85 | 9 | 64 | 2.091503 | 0.0807 | 0.876712 | 0.227273 | 0.735294 | 0.42953 |
| QT > 30 | 32 | 123 | 2 | 26 | 3.382114 | 0.1089 | 0.928571 | 0.206452 | 0.941176 | 0.174497 |

As can be seen in Table 17, an individual's KCNQ1 sequence at the SNP_A-2279707 (rs179407) locus is highly predictive of whether the individual will experience QT prolongation following the administration of iloperidone. For prolongation as did not (15). This resulted in a sensitivity (probability that the individual will have a SNP genotype associated with a predisposition to QT prolongation, given that he/she experienced QT prolongation) of 0.87 and a specificity (probability that the individual will not have a SNP genotype associated with a predisposition to QT prolongation, given that he/she did not experience QT prolongation) of 0.29, a negative predictive value (probability that the individual will not experience QT prolongation, given that he/she does not have a SNP genotype associated with a predisposition to QT prolongation) of 0.56, and a positive predictive value (probability that the individual will experience QT prolongation, given that he/she has a SNP genotype associated with a predisposition to QT prolongation) of 0.68.

The use of higher thresholds (i.e., QTs greater than 15 and 30 milliseconds) yielded markedly increased negative predictive values (0.74 and 0.94, respectively). The associated decrease in positive predictive values, from 0.68 for QTs greater than 5 milliseconds to 0.17 for QTs greater than 30 milliseconds) suggests that additional factors affect more severe QT prolongation.

As the data in Table 17 show, an individual's KCNQ1 sequence at the SNP loci above may be used to predict whether an individual is predisposed to QT prolongation due to the administration of a compound capable of prolonging the QT interval. That is, individuals having one or more SNP genotype associated with a predisposition to QT prolongation may reliably be predicted to experience a prolonged QT interval (i.e., a QT interval prolonged by at least 5 milliseconds) following the administration of a compound capable of prolonging the QT interval. Similarly, individuals not having any of the above SNP genotypes associated with a predisposition to QT prolongation may reliably be predicted to not experience severe QT prolongation (i.e., a QT interval prolonged greater than 15 milliseconds) following the administration of a compound capable of prolonging the QT interval.

Methods according to the invention may involve direct sequencing or genotyping of an individual's KCNQ1 and/or CYP2D6 genes or the characterization of expression products of the genes. For example, as noted above, the CYP2D6G1846A polymorphism results in premature termination of the CYP2D6 protein and the CYP2D6C100T polymorphism results in the substitution of a proline at position 34 by serine. Either of these polymorphisms could be determined from the resulting proteins or RNA. Accordingly, the invention includes testing genes and/or their expression products.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of administering iloperidone or a metabolite thereof to a human individual, the method comprising:
   determining or having determined the individual's KCNQ1 genotype at position 79764 of SEQ. ID. 1; and
   in the case that the individual's KCNQ1 genotype at position 79764 of SEQ. ID. 1 is associated with an increased risk of QT prolongation, administering to the individual a first quantity of iloperidone or a metabolite thereof, and
   in the case that the individual's KCNQ1 genotype at position 79764 of SEQ. ID. 1 is not associated with an increased risk of QT prolongation, administering to the individual a second quantity of iloperidone or a metabolite thereof, wherein the first quantity is less than the second quantity,
   wherein the KCNQ1 genotype associated with an increased risk of QT prolongation is GG at position 79764 of SEQ. ID. 1, and the KCNQ1 genotype not associated with an increased risk of QT prolongation is non-GG at position 79764 of SEQ. ID. 1.

2. The method of claim 1, wherein the method comprises administering iloperidone to the individual.

3. The method of claim 1, wherein the method comprises administering a metabolite of iloperidone to the individual, wherein the metabolite is 1-[4-[3-[4-(6-Fluoro-1,2-benzisoxazol-3-yl)-1-piperidinyl]propoxy]-3-methoxyphenyl]ethanol.

4. The method of claim 1, further comprising:
   Determining or having determined at least a portion of the patient's CYP2D6 genotype,
   in the case that the individual's CYP2D6G1846A genotype is AA or GA or the individual's CYP2D6C100T genotype is TT or CT, and the individual's KCNQ1 genotype is GG at position 79764 of SEQ ID NO: 1, administering to the individual the first quantity of iloperidone or the metabolite thereof, and
   in the case that the individual's CYP2D6G1846A genotype is GG or the individual's CYP2D6C100T genotype is CC, and the individual's KCNQ1 genotype is non GG at position 79764 of SEQ ID NO: 1, administering to the individual the second quantity of iloperidone or the metabolite thereof.

5. The method of claim 1, wherein the human individual is suffering from at least one condition selected from a group consisting of:
   schizophrenia, including paranoid schizophrenia, catatonic schizophrenia, disorganized schizophrenia, undifferentiated schizophrenia, and residual schizophrenia; schizoaffective disorder, depression, bipolar mania/depression, cardiac arrythmia, Tourette's Syndrome, a psychotic disorder, including brief psychotic disorder, a

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08999638B2). An electronic copy of the "Sequence Listing" will also be available from the USPTO upon request and payment of the fee set forth in 37 CFR 1.19(b)(3).

psychotic disorder not otherwise specified, a psychotic disorder due to a general medical condition, and a substance-induced psychotic disorder; a delusional disorder, and schizophreniform disorder.

6. A method of treating a human individual with iloperidone or a metabolite thereof, the method comprising:
characterizing an expression product of the individual's KCNQ1 gene; and
in the case that the characterized expression product corresponds to a KCNQ1 genotype of GG at position 79764 of SEQ. ID. 1, administering to the individual a first quantity of iloperidone or a metabolite thereof, and
in the case that the characterized expression product corresponds to a KCNQ1 genotype of non-GG at position 79764 of SEQ. ID. 1, administering to the individual a second quantity of iloperidone or a metabolite thereof,
wherein the first quantity is less than the second quantity.

7. The method of claim 6, further comprising:
characterizing an expression product of the individual's CYP2D6 gene; and
determining whether the characterized expression product corresponds to a CYP2D6 polymorphism selected from a group consisting of: CYP2D6G1846A and CYP2D6C100T.

8. A method of administering iloperidone or a metabolite thereof to a human individual suffering from long QT syndrome (LQTS), the method comprising:
determining or having determined the individual's KCNQ1 genotype at position 79764 of SEQ. ID. 1; and
administering to the individual a quantity of the iloperidone or the metabolite thereof based on the individual's KCNQ1 genotype at position 79764 of SEQ. ID. 1,
wherein a first quantity is administered to the individual in a case in which the individual has a KCNQ1 genotype of GG at position 79764 of SEQ. ID. 1, and a second quantity is administered to the individual in a case in which the individual has a KCNQ1 genotype that is non-GG at position 79764 of SEQ. ID. 1.

9. The method of claim 8, further comprising:
determining or having determined the individual's CYP2D6 genotype; and
determining whether the individual's CYP2D6 genotype corresponds to a CYP2D6 polymorphism selected from a group consisting of: CYP2D6G1846A and CYP2D6C100T.

10. The method of claim 1, wherein the second quantity of iloperidone is 24 mg/day.

11. The method of claim 6, wherein the second quantity of iloperidone is 24 mg/day.

12. The method of claim 8, wherein the second quantity of iloperidone is 24 mg/day.

13. The method of claim 1, wherein the KCNQ1 genotype not associated with an increased risk of QT prolongation is CC or CG at position 79764 of SEQ. ID. 1.

14. The method of claim 6, wherein the non-GG KCNQ1 genotype at position 79764 of SEQ. ID. 1 is CC or CG.

15. The method of claim 8, wherein the non-GG KCNQ1 genotype at position 79764 of SEQ. ID. 1 is CC or CG.

* * * * *